US00PP29926P2

(12) United States Plant Patent
Egger

(10) Patent No.: US PP29,926 P2
(45) Date of Patent: Nov. 27, 2018

(54) ***HEUCHERELLA* PLANT NAMED 'ONYX'**

(50) Latin Name: **x *Heucherella* hybrid**
Varietal Denomination: Onyx

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/731,861

(22) Filed: Aug. 15, 2017

(51) Int. Cl.
*A01H 5/02* (2018.01)

(52) U.S. Cl.
USPC ..... Plt./441

(58) Field of Classification Search
USPC ..... Plt./263.1, 441
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct x *Heucherella* plant substantially as shown and described, characterized by leaves dark red brown in spring to almost black for the rest of the year, glossy, palmately cut leaves that are sometimes puckered, a medium mounding habit with an excellent crown count, and excellent vigor.

1 Drawing Sheet

Botanical denomination: x *Heucherella* hybrid. Variety designation: 'Onyx'.

BACKGROUND OF THE INVENTION

The present invention relates to a new and distinct cultivar of x *Heucherella* and given the cultivar name of 'Onyx'. x *Heucherella* is in the family Saxifragaceae. x *Heucherella* 'Onyx' originated from a controlled cross between *Heuchera* 'B110-5' (a proprietary, unpatented, unreleased *Heuchera*), as the seed parent, and *Tiarella* '42-2' (a proprietary, unpatented, unreleased *Tiarella*), as the pollen parent.

Compared to the seed parent *Heuchera* 'B110-5', the new cultivar has cut leaves rather than shallowly lobed leaves.

Compared to the pollen parent *Tiarella* '42-2', the new cultivar has glossy black leaves rather than matte green.

Compared to x *Heucherella* 'Burnished Bronze', U.S. Plant Pat. No. 12,159, the new cultivar has thicker leaves that are much darker and cupped on margins, it is more vigorous, and the habit is larger and more mounding.

This new x *Heucherella* is uniquely characterized by:

1. leaves dark red brown in spring to almost black for the rest of the year,
2. glossy, palmately cut leaves that are sometimes puckered,
3. a medium mounding habit with an excellent crown count, and
4. excellent vigor.

This new cultivar has been reproduced only by asexual propagation (cuttings and tissue culture using growing points at the crown). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows an eight-month-old plant in the garden in part shade in late April in Canby, Oreg.

FIG. 2 shows the same plant in a garden group in mid-May in Canby, Oreg.

DETAILED PLANT DESCRIPTION

The following is a detailed description of the new x *Heucherella* cultivar based on observations of 8-month-old specimens grown in the trial field grown in part shade late September in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The *Royal Horticultural Society Colour Chart,* 5$^{th}$ edition, 2007.

Plant:

*Type*.—Herbaceous perennial.
*Form*.—Basal rosette.
*Hardiness*.—USDA Zone 4 to 9.
*Size*.—15 cm tall from top of the foliage to the ground and 40 cm wide before trailing down.
*Habit*.—Mounding with 15 crowns.
*Vigor*.—Excellent.
*Roots*.—Fibrous, freely branching, fine and White 155A in color.

Leaf:

*Type*.—Simple.
*Arrangement*.—Rosette.
*Shape*.—Broadly ovate.
*Blade size*.—Grow to 13.5 cm long and 11 cm wide.

*Lobing/division.*—3 to 5 main palmate divisions cut ¾ of the way to the main vein each with secondary lobes cut to ½ to the secondary veins.

*Venation.*—Palmate.

*Margins.*—Broadly crenate and slightly undulate.

*Apex.*—Obtuse to mucronulate.

*Base.*—Cordate, overlapping.

*Surface texture.*—Glandular hairs on both surfaces, often puckered.

*Leaf rugosity.*—Weak to medium.

*Glossiness.*—Strong.

*Petiole description.*—Grows to 13 cm long and 2.5 mm wide, with glandular hairs and Greyed Purple 187A.

*Leaf color.*—Spring topside Greyed Purple N186C with veins 187B, bottom side Greyed Purple N186C including veins; summer through winter topside Greyed Purple N186A with veins N199A, bottom side Purple N77 including veins.

Inflorescence:

*Size.*—Usually 12 cm long and 3.5 mm wide.

*Type.*—Upright to semi-upright raceme.

*Number of flowers per raceme.*—About 65.

*Density of flowers in raceme.*—Medium.

*Number of racemes.*—About 8.

*Peduncle.*—Grows to 37 cm long, 4 mm wide at base, 1 to 2 petiolate floral leaves (blades grow to 6 cm long and 5.5 cm wide, ovate, 3 main divisions and 1 to 3 lobed, tip mucronulate, margin crenate, base cordate, glandular hairs on bottom side, topside glabrous other than margins, Greyed Purple N186C, bottom side Greyed Purple N186C).

*Pedicel.*—Grows to 3 mm long, with glandular hairs, Greyed Orange 177A.

*Bloom period.*—May through June in Canby, Oreg.

Flower bud:

*Size.*—4 mm long and 2.5 mm wide.

*Description.*—Glandular puberulent, ovoid, down to side-facing.

*Color.*—Greyed Yellow 161D.

Flower:

*Type.*—Imperfect.

*Shape.*—Campanulate.

*Attitude.*—Side-facing.

*Size.*—6 mm deep and 7 mm wide.

*Petal description.*—5 in number, stellate, spatulate, 4 mm long and 1.5 mm wide, tip acuminate, base attenuate, margin entire, glabrous and Red Purple 65C on both sides.

*Calyx description.*—6 mm deep and 7 mm wide, campanulate, with 5 lobes, divided ½ way to the base, lobes 3 mm long and 2 mm wide, oblong, glandular hairs on both sides, tip obtuse, margin entire, White NN155B on both sides with tips Greyed White 156A on inside.

*Stamen description.*—10, 3 mm long, filament 3 mm long and White NN155B, anthers Greyed Orange 177A, no pollen.

*Pistil description.*—1 in number, grows to 5 mm long and 2.5 mm wide, ovaries grow to 1.5 mm long and 2.5 wide, White NN155B, beaked style 3 mm long, Red Purple 69C.

*Fragrance.*—None.

*Lastingness.*—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct x *Heucherella* plant as herein illustrated and described.

* * * * *

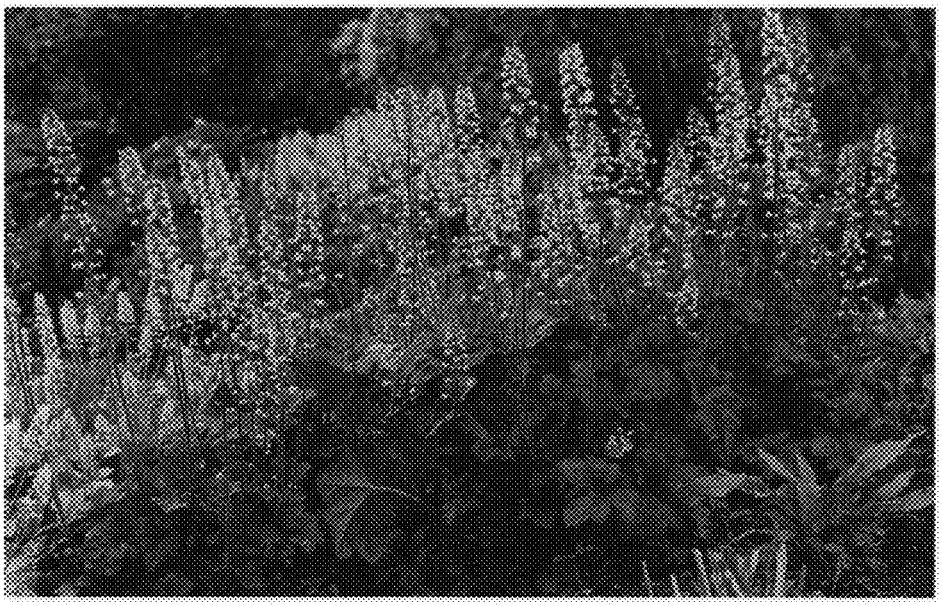

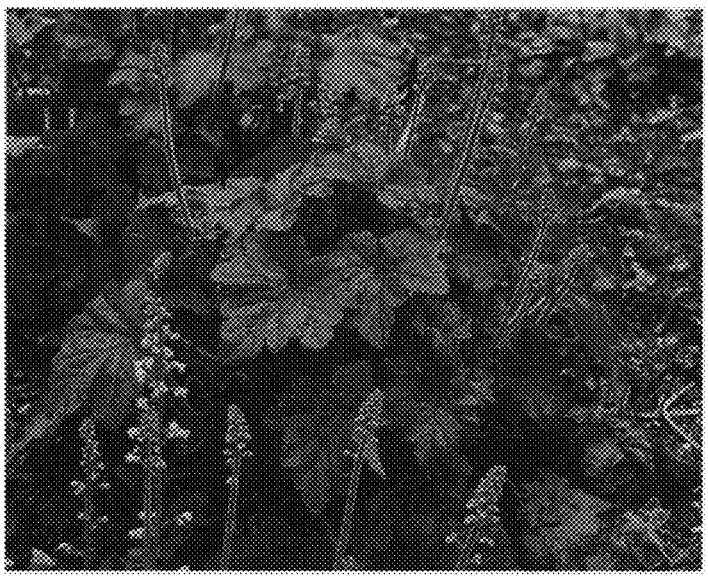
FIG. 1 above, FIG. 2 below